United States Patent
Hermann et al.

(10) Patent No.: US 7,470,826 B2
(45) Date of Patent: Dec. 30, 2008

(54) RECOVERY OF NITRATING ACID MIXTURES FROM NITRATION PROCESSES

(75) Inventors: Heinrich Hermann, Köln (DE); Jürgen Gebauer, Triosdorf (DE); Peter Konieczny, Teltow (DE); Mirko Händel, Neunkirchen-Seelsheid (DE)

(73) Assignee: Josef Meissner GmbH & Co. KG, Cologne (DE)

( * ) Notice: Subject to any disclaimer, the term of this patent is extended or adjusted under 35 U.S.C. 154(b) by 0 days.

(21) Appl. No.: 11/581,523

(22) Filed: Oct. 16, 2006

(65) Prior Publication Data

US 2007/0088183 A1    Apr. 19, 2007

(30) Foreign Application Priority Data

Oct. 18, 2005  (DE) ..................... 10 2005 050 106

(51) Int. Cl.
*C07C 201/00* (2006.01)
*C07C 205/00* (2006.01)

(52) U.S. Cl. ....................... 568/924; 568/927
(58) Field of Classification Search ............... 568/924
See application file for complete search history.

(56) References Cited

U.S. PATENT DOCUMENTS

| | | | | |
|---|---|---|---|---|
| 3,932,225 | A * | 1/1976 | Bilal et al. .................. | 205/44 |
| 4,113,975 | A * | 9/1978 | Fiege et al. ................. | 568/756 |
| 4,257,986 | A   | 3/1981 | Milligan et al. ............. | 568/934 |
| 4,511,537 | A * | 4/1985 | Fiocco et al. ............... | 422/256 |
| 4,524,077 | A * | 6/1985 | Ruest et al. ................. | 514/557 |
| 5,756,867 | A * | 5/1998 | Hermann et al. ............ | 568/934 |
| 6,143,178 | A * | 11/2000| Kostanian ................... | 210/634 |
| 6,754,979 | B2 *| 6/2004 | Ludwig et al. ............... | 34/372 |
| 6,953,869 | B2 *| 10/2005| Munnig et al. .............. | 568/934 |

FOREIGN PATENT DOCUMENTS

| EP | 0155586 A1 | 9/1985 |
|----|------------|--------|
| EP | 0279312 A3 | 4/1990 |
| EP | 0415354 A1 | 3/1991 |
| EP | 0736514 A1 | 10/1996 |

OTHER PUBLICATIONS

H. Hermann et al., "Industrial Nitration of Toluene to Dinitrotoluene", ACS Symposium Series 623, "Nitration—Recent Laboratory and Industrial Development", American Chemical Society Meeting, 1996, Washington, D.C., pp. 234-249.

Hanson, et al., "Side Reactions During Aromatic Nitration", ACS Symposium Series No. 22, Industrial and Laboratory Nitration, Division of Industrial and Engineering Chemistry, Meeting of the American Chemical Society, Philadelphia, PA, 1975, pp. 132-155.

* cited by examiner

*Primary Examiner*—Daniel M Sullivan
*Assistant Examiner*—Louisa Lao
(74) *Attorney, Agent, or Firm*—Woodard, Emhardt, Moriarty, McNett & Henry LLP

(57) ABSTRACT

The invention relates to a process for removing and recovering nitrating acid mixtures, in particular nitric acid, sulphuric acid and oxides of nitrogen, from the nitrated crude products occurring in the nitration of nitratable aromatic compounds after the nitrating acid has been separated off, by acidic scrubbing by means of a multistage extraction process, the extraction process comprising a cross-current extraction with downstream countercurrent extraction. The process permits essentially complete recovery of the abovementioned acids, including the oxides of nitrogen, in high concentrations, so that they can be recycled to the nitration and no longer pollute the wastewater.

19 Claims, 2 Drawing Sheets

RECOVERY OF NITRATING ACID MIXTURES FROM NITRATION PROCESSES

CROSS REFERENCES TO RELATED APPLICATIONS

This application claims priority to German Patent Application No. DE 10 2005 050 106.0, filed Oct. 18, 2005, entitled "RECOVERY OF NITRATING ACID MIXTURES FROM NITRATION PROCESSES", which is expressly incorporated by reference herein, in its entirety.

BACKGROUND OF THE INVENTION

The present invention relates to the removal and recovery of nitrating acid mixtures, in particular mixtures of sulphuric acid, nitric acid and oxides of nitrogen, from nitration processes. In particular, the present invention relates to a process for removing and recovering nitrating acid mixtures, in particular mixtures of sulphuric acid, nitric acid and oxides of nitrogen, which occur in the nitrated crude products in the nitration of nitratable aromatic compounds (e.g. benzene, toluene, chlorobenzene, dichlorobenzenes, mononitrobenzene, mononitrochlorobenzenes, mononitrotoluenes, dinitrotoluenes, etc.) after the nitrating acid has been separated off. According to a particular aspect, the present invention relates to a process for removing and recovering nitrating acid mixtures, in particular mixtures of sulphuric acid, nitric acid and oxides of nitrogen, from the crude dinitrotoluenes (DNT) occurring in the nitration of toluene or mononitrotoluenes (MNT) after the nitrating acid has been separated off. Furthermore, the present invention relates to a plant for the nitration of nitratable aromatic compounds with subsequent purification of the nitrated products, including removal and recovery of nitrating acid mixtures, in particular sulphuric acid, nitric acid and oxides of nitrogen.

Nitration, in particular of aromatic compounds, is one of the most prominent reactions in organic chemistry since it is of considerable industrial importance and is therefore universally used, for example in the manufacture of explosives, in the pharmaceutical industry, in the manufacture of plastics, in the production of dyes and the like. The electrophilic nitration of aromatic compounds is of particular importance for preparative chemistry, firstly because nearly all aromatics can be nitrated with a suitable nitrating reagent and secondly because the aromatic nitro group can be easily converted into other functional groups. Nitric acid/sulphuric acid mixtures (so-called "nitrating acid") with variable ratios of the two acids are the simplest and industrially most frequently used nitrating reagent. The concentrated sulphuric acid results in the formation of the actually active nitryl cation and also binds the water forming in the nitration process. For further details of the nitration, reference may be made, for example, to Römpp Chemielexikon [Römpp Chemistry Lexikon], 10th Edition, Georg Thieme Verlag, Stuttgart/New York, Volume 4, 1998, pages 2914/2915, keywords: "Nitrierung [Nitration]" and "Nitriersäure [Nitrating Acid]", and the literature referred to there in each case.

In industrial processes, considerable amounts of nitrating acid are used. Since the nitrating acid is generally used in a relatively large excess, for profitability reasons the aim is not only to remove the excess nitrating acid, including the oxides of nitrogen which are formed, from the nitrated products or to separate them off therefrom as completely as possible in order to obtain highly pure, in particular acid-free nitrating products, but also to make the isolated excess nitrating acid, including the oxides of nitrogen which are formed, capable of being used again for the nitration process and to recycle some nitrating acid with as little effort as possible. For ecological reasons too, in particular with regard to the relevant statutory regulations, it is necessary to remove the excess nitrating acid used as completely as possible and to recover it so that the pollution of the wastewater originating from the nitration process, in particular the nitrate load, can be reduced to a minimum.

Owing to the complexity of the underlying physical chemical circumstances, however, the solution of this problem is not trivial, and the prior art already contains numerous approaches and attempts for the solution of this problem, no completely satisfactory solution having as yet been found.

The complexity of the problem described above is to be illustrated below—purely by way of example—with reference to the process for the nitration of toluene or mononitrotoluenes (MNT) to dinitrotoluenes (DNT) (cf. H. Hermann et al., "Industrial Nitration of Toluene to Dinitrotoluene" in: ACS Symposium Series 623, "Nitration—Recent Laboratory and Industrial Development", Editors: L. F. Albright et al., Chapter 21, American Chemical Society, 1996, Washington D.C.), the present invention not being limited thereto but rather being generally applicable universally to processes for the nitration of nitratable aromatic compounds, for which the following statements apply accordingly.

For example, DNT can be prepared from toluene in a two-stage isothermal process by the countercurrent method, it always being necessary for an excess of 1.01 to 1.08 of the required amount of nitric acid to be present in the nitrating acids in order to achieve a quantitative conversion of the substances to be nitrated (toluene or MNT) at the respective stage. In the first nitration stage (MNT stage), toluene is selectively reacted with the DNT spent acid from the DNT stage and fresh nitric acid at temperatures between 25 and 45° C. to give MNT. The nitrating acid (MNT spent acid) occurring after the end of the reaction in the first nitration stage still contains 70 to 73% of sulphuric acid, about 0.3 to 0.7% of nitric acid and 0.4 to 2.0% of nitrous gases as $HNO_2$ in equilibrium with the organic phase. After phase separation, the MNT spent acid is fed to an MNT spent acid treatment in order to remove the remaining amount of nitric acid, the nitrous gases and the dissolved MNT/DNT. The crude MNT, which still contains nitrocresols, nitric acid, nitrous gases and other degradation products, is reacted directly without purification in the second stage with a fresh mixed acid comprising 96% of sulphuric acid and about 98% or 60 to 68% of nitric acid to give DNT. The crude DNT occurring after the nitrating acid has been separated off ("DNT spent acid") still contains nitrocresols, nitric acid, sulphuric acid and dissolved nitrogen dioxide ($NO_2$) in addition to the DNT isomer mixture comprising about 76% of 2,4-DNT, 19.5% of 2,6-DNT, 0.6% of 2,5-DNT, 3.7% of "orthoisomers" (2,3-DNT and 3,4-DNT) and 0.8% of 3,5-DNT, not more than 0.01% of MNT and traces of TNT (e.g. 0.02%) (cf. for example U.S. Pat. No. 4,482,769 A). The amount of nitric acid, sulphuric acid and nitrous gases dissolved and suspended in the crude DNT depends on the composition of the DNT spent acid and on the quality of the phase separation between the DNT spent acid and the crude DNT after the end of the reaction.

In order to remove these substances, the crude DNT occurring after the nitrating acid has been separated off after the nitration of toluene to give DNT, which crude DNT still contains sulphuric acid, nitric acid, oxides of nitrogen ("nitrous gases"), cresols and further degradation products, is freed from the abovementioned impurities by scrubbing with water in a plurality of stages. This is achieved in the prior art in a three-stage scrub by a standard process as described in terms of the basic principle, for example, in A. B. Quakenbusch and B. T. Pennington, "The Olin Dinitrotoluene (DNT) Process", Polyurethanes World Congress, 10-13 Oct. 1993: the scrubbing is carried out at 60 to 70° C. in three stages, in the first stage (acidic scrubbing) all acids, such as sulphuric acid, nitric acid and nitrous acid or nitrous gases, being washed out with water, in the second scrubbing stage (alkali scrubbing) all weakly acidic substances, such as, for example, nitrocresols, being washed out with sodium carbonate solutions, and finally, in the last scrubbing stage, the traces of sodium carbonate and cresols being removed with water. The present invention is concerned with the optimization of the first stage (acidic scrubbing).

The combined wastewaters saturated with DNT and originating from the scrubbing of the crude DNT are always acidic—owing to the high content of acids in the crude DNT—and, depending on the amount of scrubbing water (1.5 to 3 m$^3$/DNT) in relation to the scrubbed DNT, contain about 0.2 to 3.0% of sulphuric acid, 1 to 3% of nitric acid, 0.1 to 0.2% of HNO$_2$, 0.2 to 0.5% of DNT (depending on temperature and acid content), 400 to 800 ppm of nitrocresols and other degradation products from the oxidation of the nitrocresols in the DNT stage. In addition to the toxic nitrocresols, which have to be removed before the wastewater is released into a main outfall, the high content of 1 to 3% of nitric acid and of 0.2 to 3% of sulphuric acid in the wastewater also presents a problem. Both the amount of nitric acid present in the wastewater and the amount of residual nitric acid and nitrous gases present in the waste acid are lost to the nitration process and, depending on the method of treatment, are obtained as more or less dilute nitric acid which cannot be recycled directly to the nitration. Thus, a dilute nitric acid with about 16% of nitric acid is obtained from an MNT spent acid by flush evaporation in vacuo, or a two-phase mixture comprising 15 to 30% of nitric acid and MNT/DNT as the organic phase by stripping at atmospheric pressure.

Before release of these wastewaters from the acidic scrubbing of the DNT or from the purification of the MNT spent acid into a main outfall, not only the dissolved MNT/DNT but also the high nitrate and sulphate content must be reduced to the limits to be complied with or legally valid limits for the introduction of wastewaters (e.g. 50 mg/m$^3$ for nitrate, 1200 mg for sulphate and COD 175 mg of O$_2$/l). This is possible only by a treatment of the wastewater with calcium hydroxide separating off the excess sulphate as calcium sulphate, with subsequent biological degradation of the nitrate and of the organic load.

It was proposed in the prior art to carry out the removal of the acidic components from the crude DNT by means of extraction methods. However, this is not trivial. This is because, an extraction of the acidic components from the crude DNT is not a simple extraction in which a partition coefficient for the partition between the phases is effective for each component over the total concentration range, but a very complex system. All components are removed from the crude DNT by reaction with water according to equations (1) to (3) via the partition equilibrium of these components between organic phase (crude DNT) on the one hand and scrubbing with water on the other hand:

$$H_2SO_4 + H_2O \leftrightarrows H_3O^+ + HSO_4^- \quad (1)$$

$$HNO_3 + H_2O \leftrightarrows H_3O^+ + NO_3^- \quad (2)$$

$$3NO_2 + H_2O \rightarrow 2HNO_3 + NO \quad (3)$$

These equilibria according to equations (1) to (3) influence one another and do so as a function of the concentrations of the individual components. In addition, the partition equilibria between organic phase and aqueous phase depend on the concentrations of these components in the aqueous phase. At low concentrations, sulphuric acid and nitric acid are present in the completely dissociated state according to the above equations (1) and (2) in the aqueous extract; the partition coefficient between aqueous phase and organic phase is high, and the partition equilibrium between the two phases is completely on the side of the aqueous extract. The complete extraction of NO$_2$ depends on the irreversible disproportionation of NO$_2$ according to equation (3); the rate of this disproportionation is influenced by the acid strength in the aqueous phase and is equally greatly dependent on the residence time.

Because of the relevant partition equilibrium, sulphuric acid is essentially completely extracted from the organic phase up to a concentration of about 70% in the aqueous extract; essentially, no back-extraction takes place. Only from about 70% of sulphuric acid does a back-extraction into the organic phase take place with increasing concentration of the sulphuric acid. This is, for example, the reason why up to 0.7% of sulphuric acid is present in solution in the DNT in the crude DNT in equilibrium with a DNT spent acid with a sulphuric acid content of more than 81% (sulphuric acid/water ratio). On the other hand, nitric acid is present as nondissociated nitric acid in aqueous solution at relatively low concentration and is then back-extracted as such—depending on the partition equilibrium—into the organic phase. The partition coefficient for nitric acid between aqueous phase and organic phase decreases continuously with increasing concentration of the washed-out acids in the aqueous phase; this effect is greatly enhanced by the presence of sulphuric acid, so that the abovementioned partition coefficient for nitric acid between aqueous and organic phase can even assume values of less than 1 in the presence of sulphuric acid. In the mixture of sulphuric acid and nitric acid in water, the dissociation equilibrium for nitric acid according to the above equation (2) is in fact shifted, even at relatively low concentrations of nitric acid in the aqueous phase, to the side of the nondissociated nitric acid, which is preferably back-extracted into the organic phase.

The nitrogen dioxide (NO$_2$) disproportionates essentially irreversibly in the aqueous phase according to the above equation (3) to give nitric acid. However, this proportionation according to the above equation (3) also takes place only quantitatively in the presence of a large amount of water. In the presence of more highly concentrated sulphuric acids, on the other hand, the disproportionation takes place not according to equation (3) but according to the following equations (4) and (5):

$$2NO_2 + H_2O \rightarrow HNO_3 + HNO_2 \quad (4)$$

$$HNO_2 + H_2SO_4 \rightarrow H_2O + NOHSO_4 \quad (5)$$

The HNO$_2$ in equation (4) is trapped by formation of the salt NOHSO$_4$ according to the above equation (5) so that a further disproportionation to HNO$_3$ and NO according to the following equation (6):

$$3HNO_2 \rightarrow HNO_3 + 2NO + H_2O \quad (6)$$

no longer takes place or at any rate does so only very slowly.

This behaviour in particular is the reason why, in all spent acids from the nitration, nitrosyl sulphuric acid (NOHSO$_4$) is also present in addition to nitric acid from 65% sulphuric acid content upwards, which nitrosyl sulphuric acid has to be removed in the reconcentration of these spent acids, for example by complicated stripping with steam or with other methods.

These complex properties of the mixture of nitric acid, sulphuric acid and oxides of nitrogen in the crude DNT and mutual interaction thereof in the extraction make solving the problem described above more difficult.

In order to reduce the loss of nitric acid of about 8% of the amount required for the nitration and hence the effort for the removal of the nitric acid from the wastewater, it was proposed in the prior art to concentrate the dilute nitric acid, comprising about 16.3% of nitric acid and about 4.9% of $HNO_2$ and obtained, for example, in the purification of the MNT spent acid by flush evaporation, by distillation to a 65% strength nitric acid, which can be recycled to the nitration (cf. EP 0 415 354 A2).

Furthermore, according to EP 0 279 312 A2, attempts have been made to recover the nitric acid, sulphuric acid and nitrous gases dissolved or suspended in the crude DNT by scrubbing the crude DNT with up to 10% of water, so that the concentrated wash acid obtained during the scrubbing and having a density greater than that of the DNT can be recycled directly to the nitration. The aim of EP 0 279 312 A2 is therefore to achieve acid concentrations which are as high as possible by as high a DNT/wash water ratio as possible even in the combined acid extract from the two-stage extraction from crude DNT, so that the recycled acid phase can be used as mixed acid without special concentration in the first nitration stage—which, however, takes place at the expense of only incomplete recovery of nitric acid: in fact, only about 50 to 72% of the nitric acid dissolved in the crude DNT can be recovered by this procedure; the amount of 0.3 to 0.6% of nitric acid still remaining in the DNT (3-6 kg/t of DNT) furthermore passes via the scrubbing into the wastewater and constitutes a considerable pollution. Furthermore, according to EP 0 279 312 A2, no recovery of the oxides of nitrogen takes place and they are not taken into account; with regard to its procedure, the process is therefore not optimized for recovering to a sufficient degree the oxides of nitrogen which are also present and the nitric acid produced therefrom by disproportionation, which explains the relatively poor yields with respect to the recovery of nitric acid. According to Working Examples 1 and 2 of EP 0 279 312 A2, the sulphate load in the wastewater is reduced by about 96 to 97%, but the nitrate load by only about 60 or 72%: considerable amounts of nitrate still enter the wastewater (about 3.0 kg/t of DNT in Example 1 and 5.2 kg/t of DNT in Example 2), also implying a loss of nitric acid for the nitration in addition to further treatment measures for this wastewater for removing nitrates. Thus, the process described in EP 0 279 312 A2, with the alleged main aim of as quantitative a recovery as possible of the sulphuric acid from the crude DNT the obtaining of an extract with an acid concentration which is so high that, on recycling to the nitration, the nitration equilibrium with respect to the water content in the nitrating acid is shifted as little as possible to higher water contents in the nitrating acid, tacitly accepts that the recovery of nitric acid does not take place quantitatively, so that a reduction of the nitrate load in the wastewater to a minimum for avoiding additional treatment measures for the purposes of the removal of the nitrate cannot be achieved at all.

For recovery of the nitric acid from the crude DNT, further attempts were made, according to U.S. Pat. No. 4,257,986 A, to extract a part of the nitric acid from the crude DNT by scrubbing the crude DNT with a purified MNT spent acid and then to recycle this MNT spent acid laden with nitric acid to the nitration. By means of this process, the nitric acid and nitrous gases dissolved in the crude DNT cannot be extracted completely but only according to the partition equilibrium for these substances between the DNT and the acid (about 50 to 60% of the nitric acid present).

Furthermore, according to EP 0 155 586 A1, attempts were made, by changing the nitration conditions, to reduce the losses of nitric acid by extraction with the crude DNT or the formation of nitrous gases from nitric acid by oxidation with the dinitrocresols present in the crude MNT (predominantly 2,4-dinitroparacresol) by carrying out the nitration of the toluene to MNT not with about 70 to 72% but with 72 to 76% of sulphuric acid in the MNT spent acid. By means of this nitration of the toluene to MNT in an MNT spent acid having a sulphuric acid content of about 75%, up to 25% less dinitrocresol is formed than in the nitration in an MNT spent acid comprising 70% of sulphuric acid (cf. Hanson et al., ACS Symposium Series No. 22, 132 (1976), Industrial and Laboratory Nitration).

All abovementioned measures help to reduce the losses of nitric acid in the nitration of toluene to DNT by discharge from the nitration process. However, both the scrubbing of the crude DNT according to EP 0 279 312 A2 and the concentration of the nitric acid obtained from the flush evaporation of MNT spent acid according to EP 0 415 354 A2 lead, at the respective part-stages, only to a reduction of the nitric acid loss. In relation to the total process (nitration, spent acid treatment and scrubbing), wastewaters having high nitrate concentrations are still obtained.

Canadian Patent CA 1 034 603 A describes a process for the preparation of toluenediamine, in which toluene is nitrated in the presence of an inorganic acid, and the crude dinitrotoluenes thus formed, which should be free of acid-neutralizing compounds, are then scrubbed with water in order to remove the excess acids before the catalytic reduction of the dinitrotoluenes to the diamines. The total resulting aqueous extract is then obtained as wastewater. Reuse and recycling of the extract are not considered for profitability reasons in the process according to CA 1 034 603 A, because the total wash water is obtained with such a low concentration of sulphuric acid, nitric acid, nitrous acid and nitroaromatics that recycling is completely unsuitable: the wash solution is so dilute that concentration is not worthwhile; it is therefore discarded as wastewater. In addition, the dinitrocresols remain in the DNT in this process because they are not additionally removed by scrubbing with alkali before the further processing. The nitrocresols dissolved in the DNT are removed from the process without additional effort with other residues only as bottom product in the distillation of the toluenediamine (TDA) to be prepared last of all. The removal of nitric acid without recycling to the nitration process is described only as a part-step in the preparation of TDA.

All known measures of the prior art are therefore only partial solutions for avoiding the loss of nitric acid for the nitration and hence the pollution of the wastewater from a DNT plant with nitrate.

Finally, EP 0 736 514 A2 attributable to the applicant himself describes a process for removing and recovering nitric acid, sulphuric acid and oxides of nitrogen from the crude dinitrotoluenes occurring in the nitration of toluene or mononitrotoluenes after the nitrating acid has been separated off, the crude dinitrotoluenes being extracted with a dilute aqueous solution of nitric acid, sulphuric acid and nitrous acid, the density of which is lower than that of the dinitrotoluenes, in a plurality of stages by the countercurrent method, the volume ratio of the dinitrotoluenes to the aqueous solution being in each case 1:3 to 10:1, and the aqueous extract being recycled directly or after concentration to the nitration.

It is therefore the object of the invention to provide a process for removing and recovering nitrating acid, in particular mixtures of sulphuric acid, nitric acid and oxides of nitrogen, from nitration processes, and a corresponding plant for carrying out this process. The technical background of the contested patent is accordingly the removal and recovery of sulphuric acid, nitric acid and oxides of nitrogen from the nitrated crude products occurring in the nitration of nitratable aromatic compounds after the nitrating acid has been separated off, and the preferably direct recycling to the nitration process.

In particular, it is an object of the present invention to carry out the scrubbing of the nitrated crude products obtained by nitration of nitratable aromatic compounds for removal of the nitric acid, sulphuric acid and oxides of nitrogen which are dissolved therein in such a way that these acids, including the oxides of nitrogen, can be essentially completely recovered and no longer pollute the wastewater. The recovered nitrating acid should advantageously have as high an acid content as possible in order to be able to recycle the recovered acids, including oxides of nitrogen, as far as possible without concentration, to the nitration, and particularly preferably should have a composition which is as close as possible to a nitrating acid, in order to keep the amount of water additionally introduced into the nitrating mixture with the recovered acids as low as possible.

A further object of the present invention is the provision of a process for removing and recovering nitrating acid, in particular mixtures of sulphuric acid, nitric acid and oxides of nitrogen, from the crude dinitrotoluenes (DNT) obtained in the nitration of toluene or mononitrotoluenes (MNT) after the nitrating acid has been separated off.

Finally, it is a further object of the invention to further develop and to optimize the process described in EP 0 736 514 A2 attributable to the applicant himself, in particular with regard to a more versatile applicability to nitration processes in general.

The applicant has surprisingly found that the problem described above can be solved by subjecting the nitrated crude products originating from nitration processes and still containing considerable amounts of sulphuric acid, nitric acid and oxides of nitrogen or nitrous acid, after the nitrating acid mixture has been separated off, to a multistage extraction process which provides a combination of cross-current extraction with downstream countercurrent extraction.

The present invention relates—according to a first aspect of the present invention—to a process for removing and recovering nitrating acid mixtures, in particular nitric acid, sulphuric acid and oxides of nitrogen, from the nitrated crude products occurring in the nitration of nitratable aromatic compounds, after the nitrating acid has been separated off, by a multistage extraction process. Further advantageous developments of the process according to the invention form the subject of the claims. The present invention furthermore relates—according to a second aspect of the present invention—to a production plant for nitrating nitratable aromatic compounds with subsequent purification of the nitrated products, including removal and recovery of nitrating acid mixtures, in particular sulphuric acid, nitric acid and oxides of nitrogen.

The present invention thus relates—according to a first aspect of the present invention—to a process for removing and recovering nitrating acid mixtures, in particular nitric acid, sulphuric acid and oxides of nitrogen or nitrous acid, from the nitrated crude products occurring in the nitration of nitratable aromatic compounds, after the nitrating acid has been separated off, by a multistage extraction process, the extraction process comprising at least two stages, one stage of which comprises a cross-current extraction and another stage of which comprises a countercurrent extraction. As stated in the introduction to the description of the present invention, in the context of the present invention the term "nitratable aromatic compounds" is understood in particular as meaning benzene, toluene, chlorobenzene, dichlorobenzenes, mononitrobenzene, mononitrotoluenes, mononitrochlorobenzene, dinitrotoluenes, etc.

In other words, in the process according to the invention, the nitrated crude products—after the nitrating acid phase (i.e. the acidic aqueous phase) has been separated off beforehand—are subjected to acidic scrubbing by means of a multistage extraction process, the extraction process having at least two stages, one stage of which comprises a cross-current extraction and another stage of which comprises a countercurrent extraction.

In general, the countercurrent extraction is carried out after the cross-current extraction, i.e. the cross-current extraction is carried out before the countercurrent extraction. According to a preferred embodiment, countercurrent extraction and/or cross-current extraction, preferably countercurrent extraction and cross-current extraction, are carried out in each case as a liquid/liquid extraction.

The process according to the invention surprisingly makes it possible to take into account the problem described above, i.e. to take into account in particular the considerable dependence of the partition coefficient for nitric acid between aqueous and organic phase on the sulphuric acid content in the wash acid and the poor recovery rate caused thereby in the prior art with respect to nitric acid and oxides of nitrogen in the case of high acid concentrations in the wash acid, or the concentration of the wash acid prior to recycling to the nitration, which is still necessary under certain circumstances in the prior art.

The entire extraction process for substantially quantitative recovery of sulphuric acid, nitric acid and oxides of nitrogen from the nitrated crude products with minimal use of wash water, i.e. both the cross-current extraction and the countercurrent extraction, is carried out according to the invention using an acidic, generally highly concentrated wash acid. This comprises an aqueous solution of nitric acid, sulphuric acid and nitrous acid or oxides of nitrogen. This wash acid is preferably formed in situ when the nitrated crude products—after the aqueous nitrating acid phase originating from the nitration has been separated off beforehand—are brought into contact or mixed with water, because the nitrated crude products still contain considerable amounts of sulphuric acid, nitric acid and nitrous acid or oxides of nitrogen, which then partly pass over into the aqueous phase so that the acidic wash acid is formed in situ. By means of the amount of water added to the nitrated crude products and circulation of the wash acid, it is possible specifically to establish or control the desired volume ratio of nitrated crude products to wash acid (i.e. to the aqueous solution of nitric acid, sulphuric acid and nitrous acid) and the composition or concentration thereof, as described below. For this purpose, defined ranges of volume ratios crude products/wash acid or crude products/(fresh) water are advantageously maintained so that efficient and complete removal and recovery of the nitrating acid mixtures, in particular of nitric acid, sulphuric acid and nitrous acid or oxides of nitrogen, are permitted.

In general, the process according to the invention is carried out by a procedure in which the countercurrent extraction is carried out after the cross-current extraction, i.e. the cross-current extraction is effected before the countercurrent extraction. In other words, the nitrated crude product mixture to be freed from nitric acid, sulphuric acid and oxides of nitrogen is then subjected to acidic scrubbing by means of cross-current extraction, which is then followed by acidic scrubbing by means of countercurrent extraction, an aqueous solution of nitric acid, sulphuric acid and nitrous acid being used as wash acid both in the cross-current extraction and in the countercurrent extraction, but with different volume ratios of nitrated crude products to aqueous solution, as described in detail below.

The carrying out of an upstream cross-current extraction on the one hand and a downstream countercurrent extraction on the other hand is known—in each case as such—to the person skilled in the art, so that there is no need to go into further detail in this context. Besides, regarding further details in this context, reference may be made, for example, to Kirk-Othmer, Encyclopedia of Chemical Technology, Third Edition, Volume 9, John Wiley & Sons, 1980, pages 672 to 716, "Extraction liquid-liquid" and the literature cited there and to Römpp Chemielexikon [Römpp Chemistry Lexikon], 10th Edition, Georg Thieme Verlag, Stuttgart/New York, Volume 2, 1997, page 1268, key word: "Extraktion [Extraction]" and the literature cited there.

While predominantly sulphuric acid and only part of the nitric acid and the nitrous acid or the oxides of nitrogen are separated off in the cross-current extraction in the process according to the invention, the little residual sulphuric acid still remaining after the cross-current extraction and especially substantially all nitric acid still remaining after the cross-current extraction, including nitrous acid or oxides of nitrogen, are then removed in the following, second process step of countercurrent extraction. In other words, the aqueous extract originating from the cross-current extraction contains predominantly sulphuric acid and only relatively small amounts of nitric acid and nitrous acid or oxides of nitrogen, while the extract originating from the subsequent countercurrent extraction contains proportionately predominantly nitric acid and nitrous acid or oxides of nitrogen and only small amounts of sulphuric acid. The reason for this is that relatively high wash acid concentrations are used in the cross-current extraction, i.e. the amount of water added to the crude nitrated products is relatively small, which, owing to the partition equilibrium described above, means that large amounts of sulphuric acid can be removed with the wash acid but only relatively small amounts of nitric acid and nitrous acid or oxides of nitrogen: this is because the nitric acid is present as nondissociated nitric acid in aqueous solution even at relatively low concentrations and is back-extracted into the organic phase according to the partition equilibrium, this effect being seriously enhanced by the presence of sulphuric acid; nitric acid and nitrous acid or oxides of nitrogen can then, however, readily be removed in the subsequent process step of countercurrent extraction.

In general, the cross-current extraction is carried out in one stage in the present invention, whereas the countercurrent extraction is usually carried out in a plurality of stages, in particular at least two stages, preferably two to four stages, since this permits the best process economy and process efficiency.

Regarding the cross-current extraction, this is carried out—as described above—in general with an acidic wash acid, in particular with an aqueous solution of predominantly sulphuric acid and a little nitric acid or nitrous acid. The volume ratio of the nitrated crude products to the aqueous solution of nitric acid, sulphuric acid and nitrous acid (i.e. the volume ratio of nitrated crude products to wash acid) is adjusted in general to 200:1 to 1:10, in particular 120:1 to 1:5, preferably 80:1 to 1:5. Nevertheless, it may be necessary from case to case or on the basis of the application to depart from the abovementioned wash acid/nitrated crude products volume ratios, this being left to the discretion of the person skilled in the art. In general, the cross-current extraction is carried out in one stage; however, it is possible in principle to carry out the cross-current extraction in a plurality of stages, in particular two to four stages. A one-stage design of the cross-current extraction is, however, preferred according to the invention.

The adjustment of the abovementioned volume ratios in the cross-current extraction is achieved by addition of water in the appropriate amounts to the nitrated crude products and additionally by circulation of the wash acid formed in situ. Since the nitrated crude products still contain considerable amounts of sulphuric acid, nitric acid and nitrous acid, the acidic wash acid forms in situ on addition of water.

For achieving the desired concentrations of sulphuric acid, nitric acid and nitrous acid in the wash acid formed in the cross-current extraction, water is added in general in an amount of up to 10% by weight, in particular in an amount of 0.1 to 10% by weight, preferably 0.5 to 6% by weight, based on the nitrated crude products, to the nitrated crude products. The amount of water required for the cross-current extraction depends decisively on the amount of the sulphuric acid dissolved in the nitrated crude products and the nitrating acid additionally suspended and is generally chosen so that a 40 to 80% strength sulphuric acid forms during the cross-current extraction, in which sulphuric acid—depending on the partition coefficient for nitric acid and nitrous gases—small amounts of nitric acid and nitrous gases are still present in dissolved form, whereas the main amount of the nitric acid, including nitrous gases, remains in the nitrated crude products after the cross-current extraction. The water used can in principle be fresh water; according to the invention, however, it is preferable if water or condensate (e.g. vapour condensate) originating from the process itself is used, as described below; such a condensate is obtained, for example, from concentration of the aqueous extracts resulting from the countercurrent extraction or from the concentration of the sulphuric acid from the nitration. It is also possible to obtain only a part of the added water from fresh water and the other part from condensate.

The acidic aqueous extract taken off from the cross-current extraction, i.e. the acid mixture taken off from the cross-current extraction and comprising sulphuric acid, nitric acid and nitrous acid, generally has a total acid content of 40 to 80% by weight, in particular 45 to 71% by weight. The proportion of sulphuric acid here is 45 to 100%, in particular 60 to 97%, based on the total acid mixture.

In general at least 80%, in particular at least 95%, preferably at least 98%, of the sulphuric acid present in the nitrated crude products and/or at least 0.1%, in particular at least 1%, preferably at least 2%, of the nitric acid and nitrous acid present in the nitrated products, including oxides of nitrogen, are separated off by the cross-current extraction. The acidic extract resulting from the cross-current extraction or the acid mixture taken off therefrom therefore contains predominantly sulphuric acid.

The aqueous extract originating from the cross-current extraction can be fed back directly (i.e. without concentration) or after concentration, preferably directly, to the nitration. Concentration can be effected, for example, together with a nitrating spent acid originating from the nitration to give a sulphuric acid, for example comprising 87% to 96% of $H_2SO_4$, in particular in a so-called SAC plant (SAC=Sulphuric Acid Concentration).

The nitrated crude products treated by means of cross-current extraction are then fed (i.e. after removal of the acidic aqueous extract resulting from cross-current extraction) to acidic scrubbing by means of countercurrent extraction. The countercurrent extraction is carried out using an acidic wash solution, in general using an aqueous solution of nitric acid, sulphuric acid and nitrous acid. Such an acidic wash acid forms in situ by addition of the appropriate amount of water to the nitrated crude products originating from the cross-current extraction, since these still contain considerable amounts of the abovementioned acids, predominantly nitric acid and oxides of nitrogen, and additionally small amounts of sulphuric acid. In general, the volume ratio of the nitrated crude products which originate from the cross-current extraction to the wash acid (i.e. the aqueous solution of nitric acid, sulphuric acid and nitrous acid) is adjusted to values of 200:1 to 1:4, in particular 50:1 to 1:2, preferably 4:1 to 1:1, in the acidic scrubbing by means of countercurrent extraction.

For achieving or adjusting the abovementioned volume ratios in the countercurrent extraction, water (e.g. fresh water and/or condensate originating from the process) is added in the appropriate amounts to the nitrated crude products prepurified beforehand by means of cross-current extraction. The amount of water added to the nitrated crude products for the countercurrent extraction is in general 1 to 10% by weight, in particular 2 to 9% by weight, preferably 3 to 8% by weight, based on the nitrated crude products.

The aqueous acidic extract originating from the countercurrent extraction can be fed back directly (i.e. without concentration) or after concentration to the nitration. An embodiment which manages without concentration is preferred. For the case that concentration of the aqueous extract originating from the countercurrent extraction proves to be necessary, the concentration is carried out in general up to a total acid content of at least 40% by weight, in particular at least 50% by weight, preferably at least 65% by weight, calculated as nitric acid; the water or condensate originating from the concentration can then be recycled to the extraction circulation, for example to the cross-current extraction and/or to the countercurrent extraction.

The extract originating from the countercurrent extraction, i.e. the acid mixture taken off from the countercurrent extraction and comprising sulphuric acid, nitric acid and nitrous acid, generally has a total acid content, calculated as nitric acid, of 15 to 40% by weight, in particular 30 to 35% by weight.

As a result of the countercurrent extraction, the small amount of sulphuric acid still remaining after the cross-current extraction is at least substantially completely separated off; the same also applies to the nitric acid and the nitrous acid or the oxides of nitrogen, which are still present in considerable amounts in the nitrated crude products after the cross-current extraction but are removed at least substantially completely from the nitrated crude products in the countercurrent extraction.

According to a particular embodiment of the present invention, the countercurrent extraction as such can also then be carried out in a plurality of stages, in particular at least two stages, preferably two to four stages. In this particular embodiment, the volume ratio of the nitrated crude products which originate from the cross-current extraction to the aqueous solution of nitric acid, sulphuric acid and nitrous acid is adjusted to the abovementioned values of 200:1 to 1:4, in particular 50:1 to 1:2, preferably 4:1 to 1:1, in all stages of the countercurrent extraction. In this embodiment, according to which the countercurrent extraction as such is carried out in a plurality of stages, the dilute aqueous solution of nitric acid, sulphuric acid and nitrous acid, i.e. the acidic wash acid, is advantageously circulated, in particular for reasons of process economy, within each countercurrent extraction stage; this permits in particular improved phase separation and improved separation efficiency. In the particular embodiment of the multistage countercurrent extraction, in particular condensate obtained from the total process, preferably the condensate obtained in the optionally carried out concentration and/or vapour condensate obtained from the concentration of sulphuric acid from the nitration, can be added again, in addition to fresh water, to the extraction circulation of the dilute acidic solution of the last countercurrent extraction stage. In the particular embodiment of the multistage countercurrent extraction, the volume ratio of the nitrated crude products to the aqueous solution of nitric acid, sulphuric acid and nitrous acid can be adjusted by circulation and the concentration of the wash acid can be adjusted by the addition of water to the extraction circulation of the dilute solution of the last countercurrent extraction stage. For maintaining the volume ratio of the nitrated crude products to the aqueous solution of nitric acid, sulphuric acid and nitrous acid in the individual scrubbing stages (countercurrent extraction stages), after the phase separation of nitrated crude products/wash acid the wash acid separated off can be recycled to the respective scrubbing stage and only the excess fed into the next scrubbing stage.

Independently of whether the countercurrent extraction is carried out in one stage or a plurality of stages, the density of the aqueous solution of nitric acid, sulphuric acid and nitrous acid is adjusted in each case to be lower than the density of the nitrated products. This permits a reliable procedure. In contrast, depending on acid concentration, the density of the aqueous solution of nitric acid, sulphuric acid and nitrous acid may be greater than the density of the nitrated products in the upstream cross-current extraction, particularly at very high total acid concentrations. In the subsequent countercurrent extraction, however, this should be avoided for the abovementioned reasons.

The nitrated crude products resulting from the countercurrent extraction are then subjected to a further purification or treatment. This is effected in particular by means of alkali and subsequent neutral scrubbing, which in turn can optionally be followed by drying of the nitrated products.

It is completely surprising that sulphuric acid, nitric acid and oxides of nitrogen can be extracted in more than 98%, preferably more than 99%, yield from the nitrated crude products by the process according to the invention. Because of the fact that the predominant proportion of sulphuric acid is removed in the upstream cross-current extraction process step, the partition equilibrium of the nitric acid and of the nitrous acid is shifted in favour of the aqueous phase in the second, downstream process step of countercurrent extraction, so that—in addition to the residues of sulphuric acid nitric acid and nitrous acid or oxides of nitrogen can be essentially quantitatively removed in the process step of countercurrent extraction. This is possible only because of the combination, according to the invention, of acidic scrubbing by means of cross-current extraction with downstream acidic scrubbing by means of countercurrent extraction in the manner described above.

Advantageously, temperatures above the melting point of the nitrated products are employed in all extraction stages, i.e. both in the cross-current extraction and in the countercurrent extraction. In this way, the remaining acid fractions can be reliably removed from the nitrated crude products in the liquid/liquid extraction.

If concentration of the resulting, acidic aqueous extracts is intended in the cross-current extraction and/or the counter-current extraction, it is advantageous to combine the resulting solutions of nitric acid, sulphuric acid and nitrous acid, from all extraction stages, which solutions are to be concentrated, and to concentrate them together in order to feed them back to the nitration subsequently. The stripping condensates containing nitric acid and obtained from the purification of the nitrating spent acid can also be concentrated together with the solutions from all extraction stages and subsequently fed back to the nitration. The concentration is effected in general up to a total acid content of at least 40% by weight, in particular at least 50% by weight, preferably at least 65% by weight, calculated as nitric acid.

The process according to the invention is suitable in particular for removing and recovering nitric acid, sulphuric acid and oxides of nitrogen from the crude dinitrotoluenes occurring in the nitration of toluene or mononitrotoluenes after the nitrating acid has been separated off, but is by no means limited to this embodiment.

The process according to the invention permits the efficient removal and recovery of nitrating acid mixtures, in particular mixtures of sulphuric acid, nitric acid and oxides of nitrogen, from nitration processes, i.e. from the nitrated crude products, with over 98%, preferably over 99%, yield. The abovementioned acids, including the oxides of nitrogen, can be recovered essentially completely. In this way, the resulting wastewater is no longer polluted. Rather, the recovered acid mixtures can be recycled to the nitration. This is permitted according to the invention in particular because the recovered acid mixtures are obtained with relatively high concentrations, so that their recycling is directly possible. By combining cross-current extraction with downstream countercurrent extraction, the amount of water introduced is kept as small as possible, resulting in a relatively concentrated nitrating acid mixture which can optionally be recycled directly to the nitration.

The present invention furthermore relates to a production plant for nitrating nitratable aromatic compounds with subsequent purification of the nitrated products, including removal and recovery of nitrating acid mixtures, in particular nitric acid, sulphuric acid and oxides of nitrogen, the production plant comprising the following units:

a) a nitrating unit (N) for nitrating nitratable aromatic compounds, with one or more appropriate reaction containers for carrying out the nitration reaction(s); and, b) arranged in the production line downstream of the nitrating unit (N), a unit (WS) for carrying out acidic scrubbing by means of extraction, in particular for carrying out the process described above, the unit (WS) having a cross-current extraction unit (WS I) for carrying out acidic scrubbing of nitrated crude products by means of cross-current extraction and, in the production line downstream of the cross-current extraction unit (WS I), a countercurrent extraction unit (WS II) for carrying out acidic scrubbing of the nitrated crude products originating from the cross-current extraction unit (WS) by means of cross-current extraction.

A separation unit (S) for separating the acidic aqueous phase from the nitrated crude product phase is also generally provided between the nitrating unit (N) and the extraction unit (WS) before the entrance into the extraction unit (WS), before the nitrated crude products are then fed to the extraction unit (WS).

A unit (W) for further treatment and/or purification of the nitrated crude products originating from the extraction unit (WS) is also generally provided downstream of the extraction unit (WS) for the acidic scrubbing, which unit (WS) has in particular a unit (WA) for carrying out alkaline scrubbing with a downstream unit (WN) for carrying out neutral scrubbing and optionally a final unit (T) for drying of the purified end products.

With regard to the production plant according to the invention, the above statements on the process according to the invention apply in context, so that reference may be made thereto in order to avoid repetitions.

Further advantages, properties, aspects and features of the present invention are evident from the following description of a preferred working example shown in the drawings.

BRIEF SUMMARY

A process for removing and recovering nitrating acid mixtures is described, in particular nitric acid, sulphuric acid and oxides of nitrogen, from the nitrated crude products occurring in the nitration of nitratable aromatic compounds, after the nitrating acid has been separated off, by a multistage extraction process, wherein the extraction process comprises at least two stages: one stage of which comprises a cross-current extraction and another stage of which comprises a counter-current extraction.

One object of the present disclosure is to describe an improved process for removing and recovering nitrating acid mixtures.

DETAILED DESCRIPTION

Figure 1:
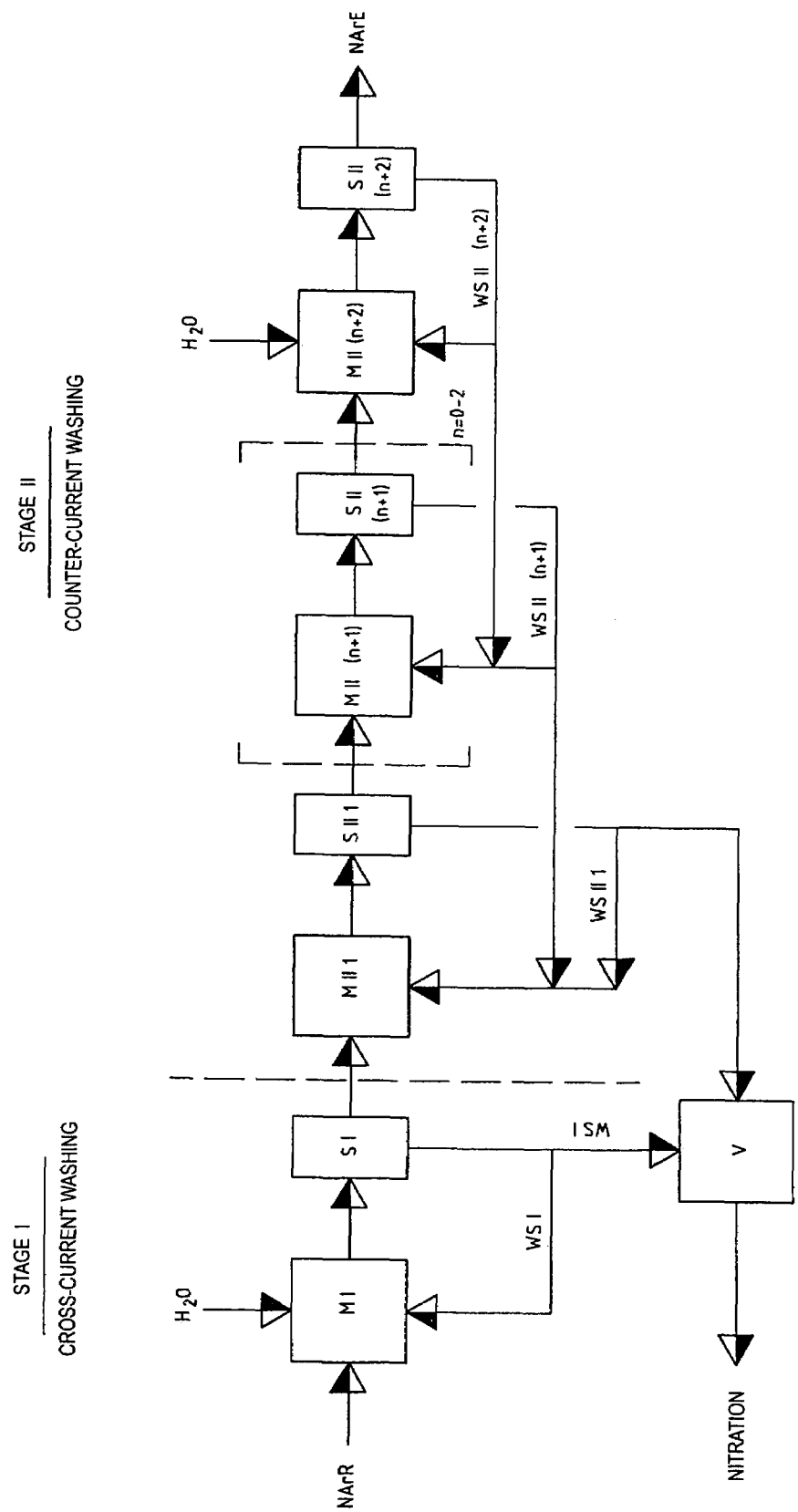
FIG. 1 shows a schematic diagram of a sequence of the process according to the invention, according to a preferred working example of the invention.

For the purposes of promoting an understanding of the disclosure, reference will now be made to the embodiments illustrated in the drawings and specific language will be used to describe the same. It will nevertheless be understood that no limitation of the scope of the disclosure is thereby intended, such alterations and further modifications in the illustrated device and its use, and such further applications of the principles of the disclosure as illustrated therein being contemplated as would normally occur to one skilled in the art to which the disclosure relates.

FIG. 1 shows an example of the process according to the invention of the two-stage scrubbing for recovering sulphuric acid, nitric acid and nitrous gases from nitroaromatics. The crude nitroaromatic (NArR) in the nitration is fed together with fresh water or condensate from an acid concentration and the circulated wash acid (WS I) from the separator (S I) in the mixer (M I) of the scrubbing stage I (cross-current scrubbing). In the separator (S I), the emulsion comprising nitroaromatic (NArR) and wash acid (WS I) is separated. The wash acid (WS I) is recycled to the mixer (M I) so that the specified wash acid:nitroaromatic volume ratio in the mixer (M I) is established. The excess of wash acid (WS I) is collected in the vessel (V). The nitroaromatic (NArR) from the separator (S I) is fed into the mixer (M II 1) of the scrubbing stage II (countercurrent extraction) together with the excess wash acid (WS II (n+1)) together with the circulated wash acid (WS II 1) from the separator (S II 1). After phase separation of the wash emulsion from the mixer (M II 1) in the separator (S II 1), the wash acid (WS II 1) is recycled to the mixer (M II 1) so that the specified nitroaromatic:water volume ratio in the mixer (M II 1) is established. The excess of wash acid (W II 1) is collected in the vessel (V) and recycled together with the wash acid (WS I) directly or after additional intermediate concentration to the nitration. The nitroaromatic (NArR) from the separator (S II 1) is fed into the mixer (M II (n+1)) together with circulated wash acid (WS II (n+1)) from the separator (S II (n+1)) and the excess of wash acid from the separator (S II (n+2)). After phase separation of the wash emulsion from the mixer (M II (n+1)) in the separator (n II+1), the wash acid (WS II (n+1)) is recycled so that the specified nitroaromatic:wash acid volume ratio in the mixer (M II (n+1)) is established. The excess of wash acid (WS II (n+1)) is fed into the mixer (M II 1). Depending on the number of scrubbing stages, this process is repeated n times. In the last mixer (M II (n+2)), the nitroaromatic to be scrubbed is fed in from the separator (S II (n+2)) together with fresh water or condensate from an acid concentration and the wash acid (WS II (n+2)) from the separator (S II (n+2)). After phase separation of the wash emulsion from the mixer (M II (n+2)) in the separator (S II (n+2)), the wash acid (WS II (n+2)) is recycled so that the specified nitroaromatic:wash acid volume ratio in the mixer (M II+(n+2)) is established. The excess of wash acid (WS II (n+2)) is fed into the mixer (M II (n+1)). The nitroaromatic (NArE) freed from acid is transferred to the following treatment with alkali.

Figure 2:
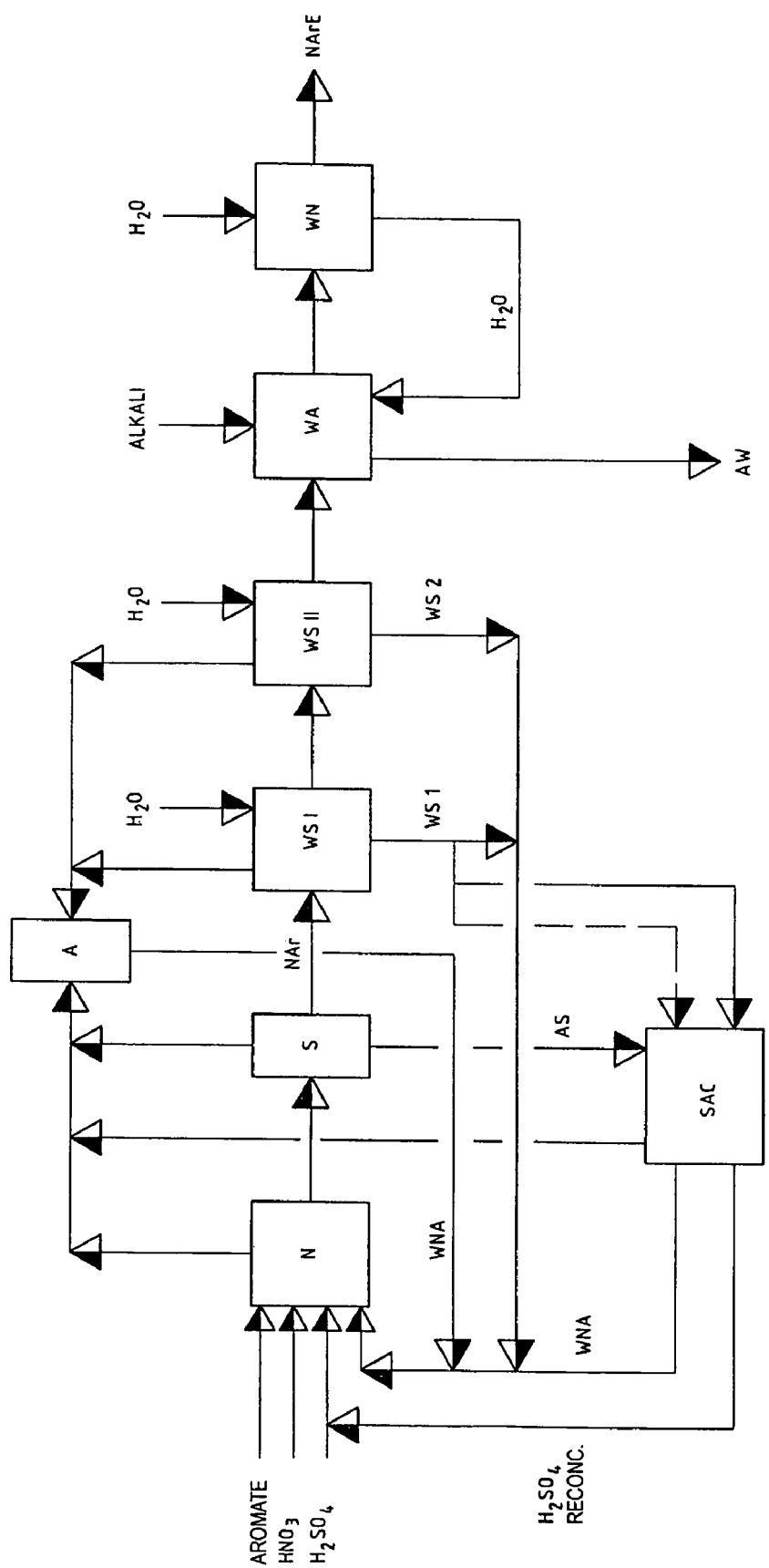
FIG. 2 shows a schematic diagram of a production plant according to the invention for nitrating nitratable aromatic compounds with subsequent purification of the nitrated products, including removal and recovery of nitrating acid mixtures, according to a preferred working example of the invention.

FIG. 2 shows an example of a plant with integrated two-stage recovery, according to the invention, of sulphuric acid, nitric acid and nitrous gases from the crude nitroaromatic. The nitroaromatic (NAr) formed in the nitrating unit (N) by the reaction of the aromatic with a mixture of nitric acid and sulphuric acid is fed, after separation of the nitrating emulsion in the separator (S), into stage 1 (cross-current scrubbing) (WS I) of the acidic scrubbing, together with water and/or condensate from the acid concentration. After phase separation of the wash emulsion in (WS I), the nitroaromatic freed from sulphuric acid is fed into stage II (countercurrent) (WS II) of the acidic scrubbing, together with the amount of water and/or condensate intended for the scrubbing and originating from an acid concentration. After phase separation of the wash emulsion in (WS II), the nitroaromatic freed from sulphuric acid, nitric acid and nitrous gases is scrubbed with alkali (WA) and then with pure water (WN). After phase separation in the neutral scrubbing (WN), the nitroaromatic (NArE) freed from acids, phenols and other impurities is transferred to the further processing (predominantly a reduction to the corresponding amines). The wash water discharged from the neutral scrubbing (WN) is fed together with alkali (e.g. sodium hydroxide solution) into the alkaline scrubbing (WA). The phenol-containing wash water (AW) separated off with alkali in the scrubbing is fed to a treatment. The wash acids WS I and WS II discharged from the acidic scrubbing in WS I and WS II according to the invention are recycled separately or together, together with the weak nitric acid (WNA) from the sulphuric acid concentration (SAC), directly or after intermediate concentration and together with the nitric acid from the waste gas purification (A) to the nitration. The wash acid from the first scrubbing stage (WS I) can alternatively also be treated together with the nitrating spent acid in the SAC plant to obtain a 87 to 96% sulphuric acid. The concentrated sulphuric acid from the SAC plant is also recycled to the nitration.

Further developments, modifications, variations and advantages of the present invention are directly recognizable and realizable by the person skilled in the art on reading the description, without departing from the scope of the present invention.

The present invention is illustrated with reference to the following example, which, however, by no means limits the present invention.

EXAMPLE

Stage I

Cross Flow Cross-Current Extraction 3400 kg of crude DNT having a residual content of 1.85% of sulphuric acid, 1.5% of nitric acid and 0.85% of nitrogen dioxide after the DNT spent acid has been separated off are scrubbed in one stage with a wash acid composed of 55.6% of sulphuric acid, 3.07% of nitric acid and 3.52% of nitrous gases (as $HNO_2$) in the DNT:wash acid volume ratio of 1:2.

At the same time, about 42 kg of water/h are added continuously so that the concentration of the wash acid is not changed by the acid extracted from the crude DNT.

98% of the sulphuric acid dissolved and emulsified in the crude DNT after the DNT spent acid has been separated off, about 6.7% of the nitric acid and about 13.5% of the nitrous gases (as $HNO_2$) are removed from the crude DNT in this scrubbing stage.

After phase separation of the wash emulsion, the wash acid is recycled to the scrubbing and the excess wash acid is collected in a vessel and recycled from there directly or together with the acid from scrubbing stage II (countercurrent extraction) to the nitration or combined with a nitrating spent acid originating from the nitration and subsequently treated in an SAC plant.

The crude DNT separated off (about 3335 kg of DNT/h) having a content of about 1.43% of nitric acid, 0.7% of nitrogen dioxide and 0.04% of sulphuric acid is further treated in the subsequent stage II (countercurrent extraction).

Stage II

Countercurrent Extraction

About 3335 kg of crude DNT from stage I (cross-current extraction) having a content of 0.37 kg of sulphuric acid, about 14 kg of nitric acid and about 7.35 kg of nitrogen dioxide per metric ton of crude DNT are scrubbed in two stages by the countercurrent method.

In the first scrubbing stage, the countercurrent extraction carried out in two stages altogether, the crude DNT is scrubbed with a wash acid composed of 34.22% nitric acid, 0.63% of sulphuric acid and 0.43% of nitrous gases (as $HNO_2$) in the volume ratio 1:1. At the same time, wash acid having a lower acid concentration is fed in from the second scrubbing or extraction stage of the countercurrent extraction in an amount such that the concentration in the first scrubbing stage does not change.

In the second scrubbing stage of the countercurrent extraction, scrubbing is effected, likewise with the phase ratio 1:1, with a wash acid having the concentration with which this wash acid is transferred from this scrubbing stage into the first scrubbing stage of the countercurrent extraction.

The amount of added water (about 128 l of water in the present example) which is fed in at the last extraction stage of the countercurrent scrubbing is chosen so that the concentration of the wash acid in the first extraction stage in contact with the DNT to be scrubbed does not exceed the acid strength specified for this wash acid or the specified density.

In order to maintain the desired volume ratio of 1:2 (stage I—cross-current extraction) or 1:1 (stage II—countercurrent extraction) in each scrubbing stage, the wash acid flowing from the separation part, for example of a mixer-settler, after separation of the phases is fed back into the scrubbing part as wash acid.

The excess wash acid from the extraction stage of the countercurrent extraction is collected in the same vessel as the wash acid from the cross-current extraction. The combined acid extracts having a total acid content of about 50% (calculated as nitric acid) are recycled directly to the nitration or may be additionally concentrated in a distillation apparatus to an acid concentration of not more than 65% total acid (calculated as nitric acid) before being recycled to the nitration. Alternatively, the excess wash acid from the first scrubbing stage of the countercurrent extraction can, however, also be collected separately and recycled directly to the nitration or concentrated together with the dilute nitric acid from the purification of the nitrating spent acid in a distillation apparatus to an acid concentration of not more than 65% total acid (calculated as nitric acid).

The vapour condensate with about 0.3 to 1% of acid (especially nitric acid) is recycled as wash acid to the second or last scrubbing stage of the countercurrent extraction.

In addition to the sulphuric acid, all nitrogen-containing acids ($HNO_3$ and $HNO_2$) are scrubbed out to a degree of more than 98% from the scrubbed DNT and are thus available for recycling to the nitration.

While the preferred embodiment of the invention has been illustrated and described in the drawings and foregoing description, the same is to be considered as illustrative and not restrictive in character, it being understood that all changes and modifications that come within the spirit of the invention are desired to be protected.

The invention claimed is:

1. An extraction process for removing and recovering nitrating acid mixtures, including nitric acid, sulphuric acid and oxides of nitrogen from the nitrated crude products occurring in the nitration of nitratable aromatic compounds, after the nitrating acid has been separated off, said extraction process comprising the following steps:
   performing as a first phase of said extraction process a single stage, cross-current extraction step;
   performing as a second phase of said extraction process a countercurrent extraction step carried out in a plurality of stages; and
   wherein said countercurrent extraction step is carried out after the cross-current extraction step, the cross-current extraction step and the countercurrent extraction step being carried out each as a liquid/liquid extraction step.

2. The extraction process according to claim 1, wherein the cross-current extraction step is carried out using an aqueous solution of nitric acid, sulphuric acid and nitrous acid, the volume ratio of the nitrated crude products to the aqueous solution of nitric acid, sulphuric acid and nitrous acid being adjusted to 200:1 to 1:10.

3. The extraction process according to claim 2, wherein the adjustment of the volume ratio in the cross-current extraction step is effected by addition of water in appropriate amounts to the nitrated crude products and/or by circulation of the aqueous solution of nitric acid, sulphuric acid and nitrous acid, the amount of added water being up to 10% by weight based on the nitrated crude products.

4. The extraction process according to claim 1, wherein the aqueous extract originating from the cross-current extraction step is fed back directly or after concentration to the nitration.

5. The extraction process according to claim 1, wherein the acid mixture taken off from the cross-current extraction step and comprising sulphuric acid, nitric acid and nitrous acid has a total acid content of 40 to 80% by weight.

6. The extraction process according to claim 1, wherein at least 80% of the sulphuric acid present in the nitrated crude products is separated off by the cross-current extraction step and wherein at least 0.1% of the nitric acid and nitrous acid, including oxides of nitrogen, present in the nitrated crude products is separated off by the cross-current extraction step.

7. The extraction process according to claim 1, wherein the countercurrent extraction step is carried out using an aqueous solution of nitric acid, sulphuric acid and nitrous acid, the volume ratio of the nitrated crude products from the cross-current extraction step to the aqueous solution of nitric acid, sulphuric acid and nitrous acid being adjusted to 200:1 to 1:4.

8. The extraction process according to claim 7, wherein the adjustment of the volume ratio in the countercurrent extraction step is effected by addition of water in appropriate amounts to the nitrated crude products and/or by circulation of the aqueous solution of nitric acid, sulphuric acid and nitrous acid, the amount of added water being 1 to 10% by weight based on the nitrated crude products.

9. The extraction process according to claim 1, wherein the acid mixture taken off from the countercurrent extraction step and comprising sulphuric acid, nitric acid and nitrous acid has a total acid content, calculated as nitric acid, of 15 to 40% by weight.

10. The extraction process according to claim 1, wherein at least 97% of the sulphuric acid still present in the nitrated crude products after the cross-current extraction step is separated off by the countercurrent extraction step and wherein at least 95% of the nitric acid and nitrous acid, including oxides of nitrogen, still present in the nitrated crude products after the cross-current extraction step is separated off by the countercurrent extraction step.

11. The extraction process according to claim 1, wherein the volume ratio of the nitrated crude products to an aqueous solution of nitric acid, sulphuric acid and nitrous acid being adjusted to 200:1 to 1:4 in all stages of the countercurrent extraction step.

12. The extraction process according to claim 11, wherein the aqueous solution of nitric acid, sulphuric acid and nitrous acid is circulated within each countercurrent extraction step stage.

13. The extraction process according to claim 11, wherein a condensate occurring in the case of concentration is added to the extraction circulation of a dilute solution of the last countercurrent extraction step stage.

14. The extraction process according to claim 11, wherein the volume ratio of the nitrated crude products to the aqueous solution of nitric acid, sulphuric acid and nitrous acid is adjusted by the addition of water to the extraction circulation of the aqueous solution of the last countercurrent extraction step stage and wherein, for maintaining the volume ratio of the nitrated crude products to the aqueous solution of nitric acid, sulphuric acid and nitrous acid in the individual countercurrent extraction step stages after the phase separation of nitrated crude products/wash acid, the wash acid separated off is recycled to the respective countercurrent extraction step stage and only the excess is fed into the next countercurrent extraction step stage.

15. The extraction process according to claim 1, wherein the countercurrent extraction step is carried out in such a way that the density of the aqueous solution of nitric acid, sulphuric acid and nitrous acid is adjusted in each case to be lower than the density of the nitrated products.

16. The extraction process according to claim 1, wherein the countercurrent extraction step produces an aqueous extract which is fed back directly or after concentration to the nitration, in the case of concentration the concentration being carried out to a total acid content of at least 40% by weight calculated as nitric acid, and wherein the nitrated crude products treated by means of countercurrent extraction step are then fed to a further purification or treatment by means of alkali and subsequent neutral scrubbing, optionally with subsequent drying.

17. The extraction process according to claim 1, wherein a temperature above the melting point of the nitrated products is employed in all extraction stages and wherein all extraction stages are carried out in each case as liquid/liquid extractions.

18. The extraction process according to claim 1, wherein the resulting solutions of nitric acid, sulphuric acid and nitrous acid from all extraction stages are combined and are concentrated together to a total acid content of at least 40% by weight calculated as nitric acid, in order to be subsequently recycled to the nitration.

19. The extraction process according to claim 1, wherein the process is used for removing and recovering nitric acid, sulphuric acid and oxides of nitrogen from the crude dinitrotoluenes occurring in the nitration of toluene or mononitrotoluenes after the nitrating acid has been separated off.

* * * * *

UNITED STATES PATENT AND TRADEMARK OFFICE
CERTIFICATE OF CORRECTION

PATENT NO. : 7,470,826 B2
APPLICATION NO. : 11/581523
DATED : December 30, 2008
INVENTOR(S) : Heinrich Hermann et al.

It is certified that error appears in the above-identified patent and that said Letters Patent is hereby corrected as shown below:

Column 18, line 26, the word "countercurrent" should be replaced with --cross-current--

Column 18, line 30, the number "1" should be replaced with the word --up--

Signed and Sealed this

Twenty-fourth Day of February, 2009

JOHN DOLL
*Acting Director of the United States Patent and Trademark Office*